United States Patent
Bruder

(10) Patent No.: US 7,693,253 B2
(45) Date of Patent: Apr. 6, 2010

(54) METHOD AND CT UNIT FOR TAKING X-RAY CT PICTURES OF A PATIENT'S BEATING HEART

(75) Inventor: Herbert Bruder, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 34 days.

(21) Appl. No.: 11/349,129

(22) Filed: Feb. 8, 2006

(65) Prior Publication Data

US 2006/0241403 A1 Oct. 26, 2006

(30) Foreign Application Priority Data

Feb. 9, 2005 (DE) ........................ 10 2005 005 919

(51) Int. Cl.
*A61B 6/00* (2006.01)
(52) U.S. Cl. .............................................. 378/8; 378/4
(58) Field of Classification Search ................ 378/4, 378/8, 901; 600/425
See application file for complete search history.

(56) References Cited

U.S. PATENT DOCUMENTS

| | | | |
|---|---|---|---|
| 3,557,371 A | * | 1/1971 | Becker .......................... 378/95 |
| 4,506,678 A | * | 3/1985 | Russell et al. ................ 600/536 |
| 4,519,395 A | * | 5/1985 | Hrushesky ................... 600/484 |
| 5,924,980 A | * | 7/1999 | Coetzee ....................... 600/300 |
| 6,415,174 B1 | * | 7/2002 | Bebehani et al. ............ 600/513 |
| 6,434,215 B1 | * | 8/2002 | Cesmeli .......................... 378/8 |

(Continued)

FOREIGN PATENT DOCUMENTS

WO WO 02/26125 * 9/2001

(Continued)

OTHER PUBLICATIONS

Kachelrieb et al., Kymogram detection and kymogram-correlated image reconstruction from subsecond spiral computed tomography scans of the heart, Med. Phys., 29(7), Jul. 2002, pp. 1489-1503.*

(Continued)

*Primary Examiner*—Edward J Glick
*Assistant Examiner*—Alexander H Taningco
(74) *Attorney, Agent, or Firm*—Harness, Dickey & Pierce, P.L.C.

(57) ABSTRACT

A method and a CT unit are disclosed for taking cardio X-ray CT pictures, in the case of which a synthetic clock signal is used to display a clock, during each cycle phase of the synthetic clock signal. Test volume data records of the heart are reconstructed at a number of different phase instants of the synthetic clock over the complete scan, which are respectively associated with their phase instants and their z-position. Subsequently, a correlation calculation between test volume data records that are temporally neighboring and spatially identical or at least belong to the same slice plane are used to determine maxima of the correlation. Finally, imaging volume data records are subsequently calculated from the spatiotemporally associated detector data.

18 Claims, 2 Drawing Sheets

U.S. PATENT DOCUMENTS

| | | | |
|---|---|---|---|
| 6,780,152 B2 * | 8/2004 | Ustuner et al. | 600/443 |
| 6,937,696 B1 * | 8/2005 | Mostafavi | 378/95 |
| 7,031,504 B1 * | 4/2006 | Argiro et al. | 382/131 |
| 2003/0048867 A1 * | 3/2003 | Acharya et al. | 378/18 |
| 2003/0174804 A1 * | 9/2003 | Bulkes et al. | 378/8 |
| 2005/0002549 A1 * | 1/2005 | Nay et al. | 382/130 |
| 2005/0201509 A1 * | 9/2005 | Mostafavi et al. | 378/8 |

FOREIGN PATENT DOCUMENTS

WO      WO 02/26125 A2    4/2002

OTHER PUBLICATIONS

Manzke et al., Automatic phase point determination for cardiac CT imaging, Medical Imaging, 2004, Proceedings of SPIE, vol. 5370, 2004, pp. 690-700.*

R.Manzke et al.: "Automatic phase point determination for cardiac CT imaging", Medical Imaging 2004: Image Processing, Proceedings of SPIE vol. 5370, S.690-699.

Th.Flohr, B.Ohnesorge: "Heart Rate Adaptive Optimization of Spatial and Temporal Resolution for Electrocardiogram-Gated Multislice Spiral CT of the Heart", Journal of Computer Assisted Tomography, vol. 25. No. 6, 2001, S.907-923.

* cited by examiner

METHOD AND CT UNIT FOR TAKING X-RAY CT PICTURES OF A PATIENT'S BEATING HEART

The present application hereby claims priority under 35 U.S.C. §119 on German patent application number DE 10 2005 005 919.8 filed Feb. 9, 2005, the entire contents of which is hereby incorporated herein by reference.

FIELD

The invention generally relates to a method and/or a computed tomography unit for taking X-ray CT pictures of a patient's beating heart, exclusive use being made for the purpose of finally taking the CT pictures of detector data that are extracted from phase sections of the cardiac cycle in the case of which the heart is relatively at rest. As a result, motional blurring leading to reduced quality pictures is reduced or even avoided.

BACKGROUND

A method is described, for example, in the document: Automatic phase point determination for cardiac CT imaging, Manzke et al., medical imaging 2004, proc. of SPIE vol. 537, 690-699. A proposal is made there that reconstructs the heart volume, on the basis of the ECG signal, in consecutive time intervals, and determines slicewise image correlations in neighboring cardiac phases. If these image correlations are plotted three-dimensionally a z/t-plane (z corresponding to the system axis, t corresponding to the percentage value of the cardiac phases under consideration), the rest phases of the heart are then manifested in this spatiotemporal display as extreme values of the correlation coefficients. Such extreme values can be detected by known computational methods such that the instants of the cardiac phase when the heart is at rest are determined. CT pictures corresponding to these time intervals are then reconstructed from the detector data according to the rest phases thus found.

A complication here is that it is necessary in each case to apply an ECG lead for the CT examination.

SUMMARY

It is an object of at least one embodiment of the invention to find a simplified method for taking X-ray CT pictures of a patient's beating heart, the aim being to dispense with picking off the patient's ECG signal.

The inventor has realized that it is possible to dispense with the patient's ECG signal and to make use, instead of a synthetic clock signal in terms of which the determination of the rest phase in each cycle is oriented. Since this synthetic clock signal is admittedly situated in the region of the patient's heart rate, but is not synchronized therewith, it is impermissible to make a determination, over all the cycles of the scan as in the method previously cited, on the general cardiac phase instant when the heart is in a rest situation.

However, it is necessary to determine over the entire scanning time and for each synthetic cycle the particular instant or precise time interval when a rest phase is present. This can be performed by calculating a multiplicity of images over the scan and also over each cycle by calculating the correlation coefficients for a prescribed image area between temporally neighboring CT images, and searching for maxima of the correlation coefficients. If the correlation coefficient of the image values is a maximum between two images, that is to say there are only slight summary variations present between the images in the area under examination, it is possible to assume a rest phase in this time range.

This time range of the respective clock cycle found in such a way and the detector data originating therefrom can now be used for the final calculation of high-value CT images. Moreover, it is to be borne in mind that when determining the correlation coefficient use is made not of the complete CT image, but exclusively of a prescribed area in the CT image so that a change in the correlation values becomes sufficiently clear.

In accordance with at least one embodiment of the invention, the inventor proposes a method for taking X-ray CT pictures of a patient's beating heart that has the following method steps:

at least one X-ray source is located relative to and around the patient in order to scan the latter, at least one detector continuously detects the attenuation of the X-rays and outputs it as detector output data to a control and arithmetic unit, a synthetic clock signal is output at a frequency that corresponds to a typical heart rate of the patient, during each cycle phase of the synthetic clock signal, test volume data records of the heart are reconstructed at a number of different phase instants of the synthetic clock over the complete scan, each test volume record being associated with its phase instant and its z-position, over a prescribed image area, correlation values are calculated between test volume data records that are temporally neighboring and spatially identical or at least belong to the same slice plane, and are entered in a spatiotemporal matrix, and a search is made for maxima of the correlation values, final volume data records are subsequently calculated from the detector data records from which the test volume data records that led to correlation maxima originate.

For the purpose of reducing the arithmetic capability, it is preferably proposed to calculate the test volume data records with a reduced resolution by comparison with the final volume data records.

Furthermore, the synthetic clock signal can also be derived from a synthetic ECG.

The prescribed image area for calculating the correlation values preferably exclusively includes the heart region here, it being possible to define the boundary in a simple way by a rectangle, square or else by a circular delimitation.

The inventive method of at least one embodiment can basically be used in conjunction both with spiral scanning and with sequential scanning.

Furthermore, the method according to at least one embodiment of the invention can be used for three different reconstruction methods: firstly, for a method in which for the final reconstruction per heart cycle a plane of respectively completed detector data is extracted from said heart cycle, and the image plane is reconstructed to form a volume data record. Again, for a method in which for the final reconstruction incomplete detector data from a number of cardiac cycles are combined to form completed detector data, and the volume data records are subsequently reconstructed therefrom. Finally, for a method in which for the final reconstruction incomplete detector data from a number of cardiac cycles are reconstructed to form incomplete image data and are subsequently combined to form complete image data.

In the case of the above-named variant methods, the actual rest phase is calculated in relation to the artificial clock signal individually for each cycle itself.

According to at least one embodiment of the basic idea outlined above, the inventor also proposes a computed tomography unit for taking X-ray CT pictures of a patient's beating heart that includes:

an apparatus for rotating scanning of the patient having at least one X-ray source and at least one detector that continuously detects the attenuation of the X-rays and outputs it as detector output data to a control and arithmetic unit, means for generating a synthetic clock signal with a frequency that corresponds to a typical patient's heart rate, means for reconstructing test volume data records of the heart during the complete scan and during each cycle phase of the synthetic clock signal at a number of different phase instants of the synthetic clock, each test volume record being associated with its phase instant and its z-position, means for calculating correlation values between temporally and spatially neighboring test volume data records over a prescribed image area and insertion in a spatiotemporal matrix that also searches for maxima of the correlation values, and means that calculates final volume data records from the detector data records from which the test volume data records that have led to correlation maxima originate, and outputs them as a three-dimensional pictorial illustration.

In the case of the above described computed tomography unit, the specified means can constitute a system of at least one arithmetic unit and programs or program modules that execute the above-described steps during operation.

BRIEF DESCRIPTION OF THE DRAWINGS

Aspects of the invention are described in more detail below with reference to an example embodiment with the aid of a single figure, the following reference symbols being used: 1: computed tomography system; 2: X-ray tubes; 3: detector; 4: system axis; 5: housing; 6: displaceable patient couch; 7: patient; 8: clock generator for pulse simulation; 9: control and arithmetic unit; 10: control and data line; $Prg_1$-$Prg_n$: computer programs.

DETAILED DESCRIPTION OF THE EXAMPLE EMBODIMENTS

Figure 1:
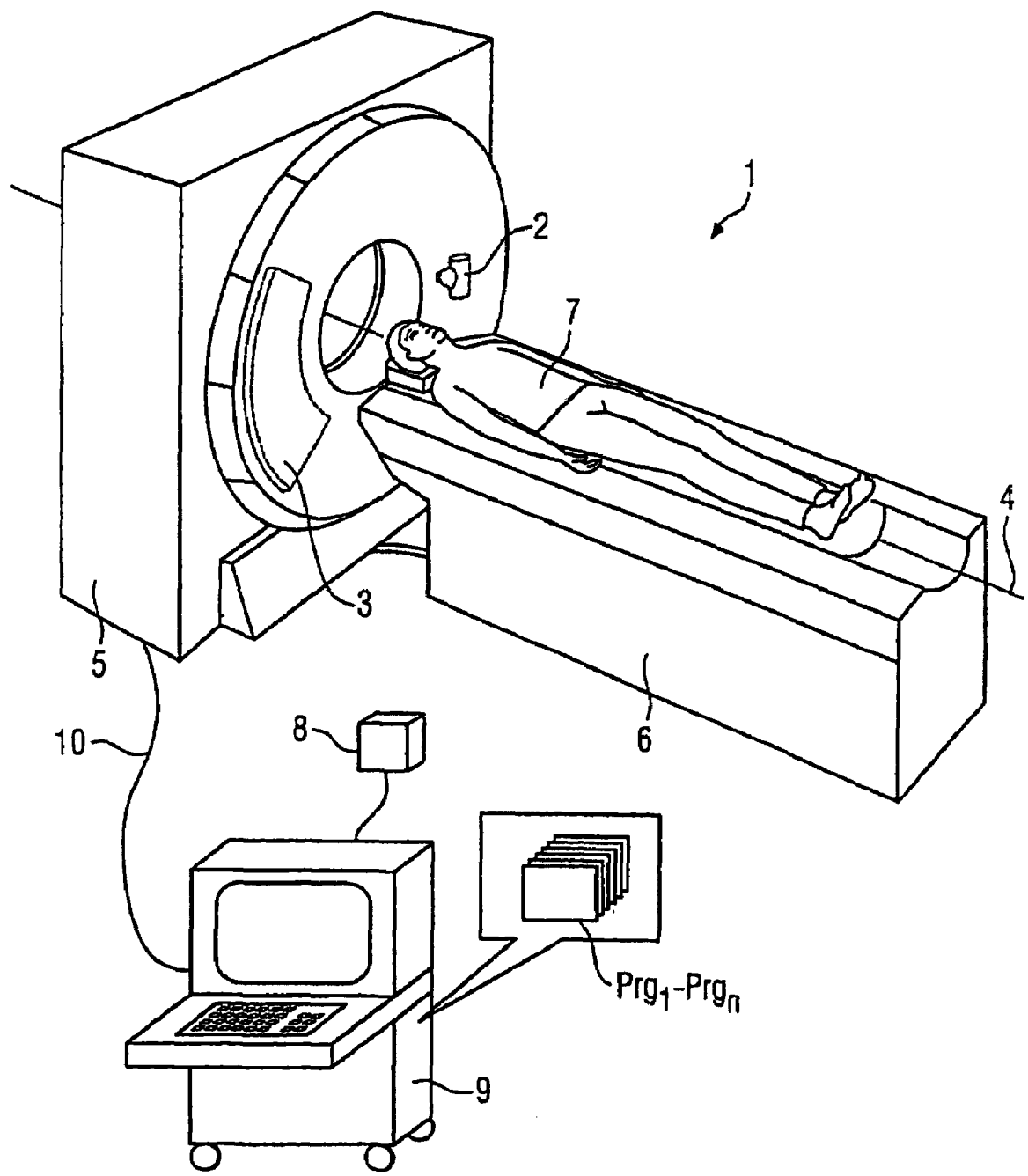
FIG. 1 shows an illustration of an example computed tomography for carrying out the method according to at least one embodiment of the invention.

FIG. 1 shows a computer tomograph 1 having a housing 5 in which there are located a gantry with a circularly revolving X-ray tube 2 and a multirow detector 3 situated opposite. Also illustrated is a patient 7 who is lying on a patient couch 6 and is moved into the opening of the CT 1 for the scanning operation. During the scanning operation, in which the X-ray tube 2 moves in a circle around the patient, a relative movement of the patient in the direction of the system axis 4 can take place such that spiral scanning takes place relative to the patient, or the patient can also be scanned by being pushed forward sequentially during a scanning pause in many purely circular movements of the tube relative to the patient.

The computer tomograph 1 is controlled by the control and arithmetic unit 9 via the control and data line 10. The data collected by the detector 3 are also transmitted to the computer via the control and data line 10. The control and arithmetic unit 9 has an internal memory and arithmetic processors via which the programs $Prg_1$-$Prg_n$ for controlling the computer tomograph and for evaluating the collected data are executed. Moreover, a keyboard for data input and a monitor for displaying data are connected to the arithmetic unit 9.

Furthermore, there is connected to the control and arithmetic unit 9 a clock generator 8 that is used as a synthetic ECG signal. When the cardio scan is being carried out, the detector data are collected and their temporal relationship with the synthetic clock is adhered to. Subsequently, a multiplicity of CT tomograms or volume data records are calculated with coarse resolution, and correlation values of the temporally offset coarse images are calculated with reference to a prescribed region in the coronary zone. Low correlation values indicate a large variation from one image to the next image, that is to say a movement situation, while high correlation values indicate that the region under investigation is at a standstill, that is to say a rest phase.

It is to be pointed out in this case that because of the continuously varying phase shift occurring between the actual cardiac rhythm and the synthetic clock no generalized statement can be made concerning the cycle phase in which the rest phase is located. The rest phase range must be determined separately for each cycle.

Once the time ranges of the rest phases are determined, exclusive use is made of the data collected there in order to calculate the final and now highly resolved volume data records or tomograms. In this case, there are various ways of using the detected data for the reconstruction. For example, given a sufficiently fast scanning rate it is possible for images to originate respectively from data of only one cycle. However, it is also possible for detector data to be assembled from two or more cycles in order to obtain complete detector data and to reconstruct image data. Moreover, it is also possible for incomplete detector data—data from less than a π revolution from the determined rest phases firstly to be reconstructed to form incomplete images or volume data records, and subsequently to assemble such incomplete images or volume data records from a number of cycles, possibly in a weighted fashion, to form complete images or volume data records.

By comparison with the known methods, there is the substantial advantage with all these variants that the complicated application of ECG electrodes can be dispensed with for the purpose of examination, and also that of avoiding problems of reading out the ECG signals such as occur, for example, owing to the requisite long lines and the electromagnetic irradiation they cause, or to falsifications of the signals through muscle contractions of the patient.

Figure 2:
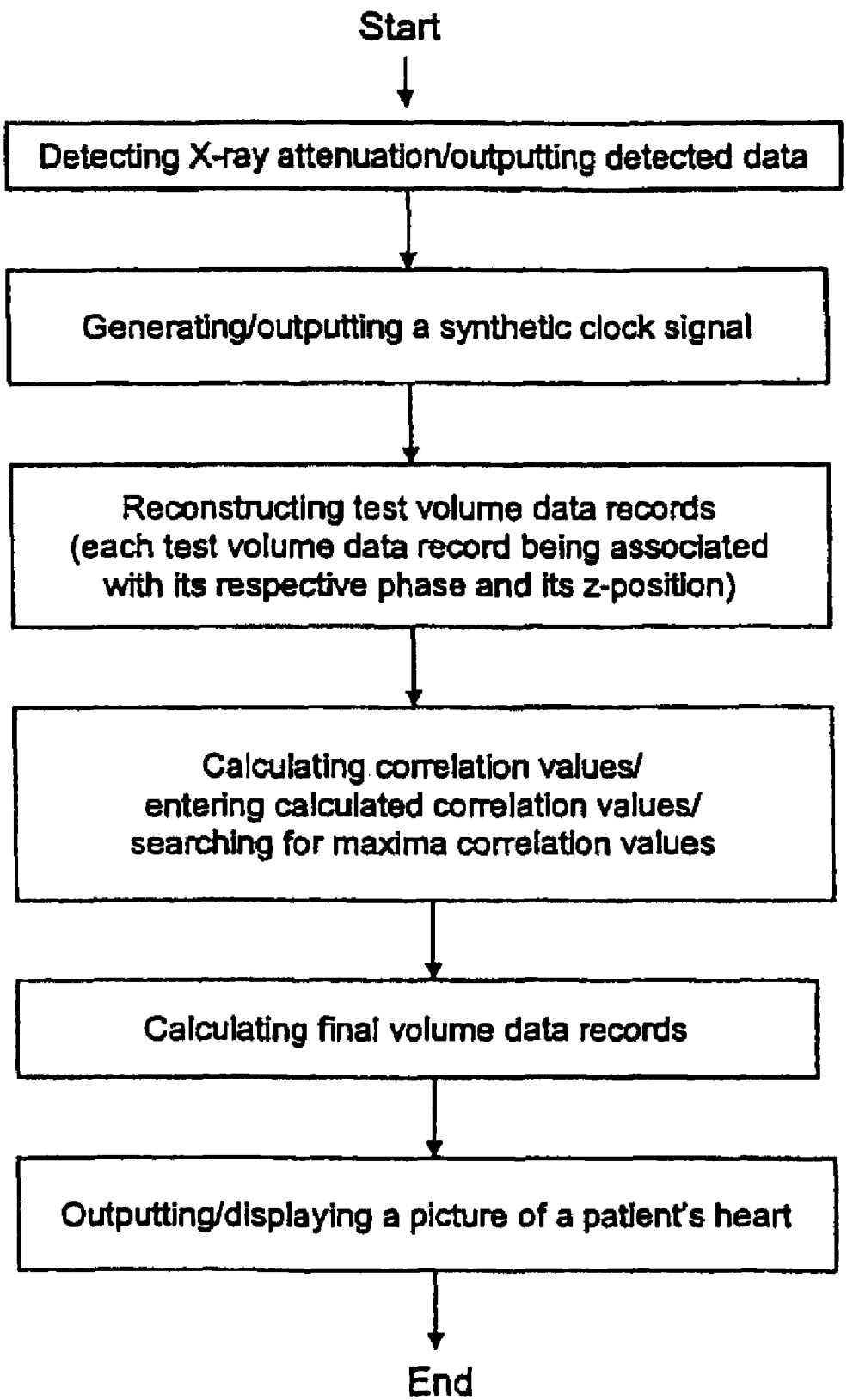
FIG. 2 shows a flowchart of an exemplary for carrying out a method according to at least one embodiment of the invention.

Thus, overall, at least one embodiment of this invention presents a method (FIG. 2) and a CT unit for taking cardio X-ray CT pictures in the case of which a synthetic clock signal is used for displaying a clock, during each cycle phase of the synthetic clock signal test volume data records of the heart being reconstructed at a number of different phase instants of the synthetic clock over the complete scan, that are respectively associated with their phase instants and their z-position, subsequently using a correlation calculation to determine the maxima of the correlation between test volume data records that are temporally neighboring and spatially identical or at least belong to the same slice plane, and subsequently calculating imaging volume data records from the spatiotemporally associated detector data.

It goes without saying that the abovementioned features of at least one embodiment of the invention can be used not only in the respectively specified combination, but also in other combinations or on their own, without departing from the scope of the invention.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for taking X-ray CT pictures of a patient's beating heart using at least one X-ray source located relative to and around the patient to scan the patient, comprising:
   detecting, via at least one detector, an attenuation of the X-rays and outputting detected data to a control and arithmetic unit;
   generating a synthetic clock signal that is not based on signals derived from the patient's beating heart;
   outputting the synthetic clock signal at a frequency that corresponds to a typical heart rate of the patient;
   reconstructing, during each cycle phase of the synthetic clock signal, test volume data records of the heart at a number of different phases of the synthetic clock over a complete scan, each test volume data record being associated with its respective phase and its z-position;
   calculating, over a prescribed image area, correlation values between test volume data records that are temporally neighboring and spatially identical or at least belong to the same slice plane, entering the calculated correlation values in a spatiotemporal matrix, and searching for maxima of the correlation values;
   subsequently calculating final volume data records from the detector data records from which the test volume data records, that led to correlation maxima, originate to obtain a final reconstruction of the data; and
   displaying a picture of the patient's heart based on the final reconstruction of the data.

2. The method as claimed in claim 1, wherein the test volume data records are calculated with a resolution that is reduced by comparison with the final volume data records.

3. The method as claimed in claim 2, wherein the prescribed image area for calculating the correlation values exclusively comprises the heart region.

4. The method as claimed in claim 2, wherein the prescribed image area is determined by a pattern recognition method and for calculating the correlation values exclusively comprises the heart region.

5. The method as claimed in claim 1, wherein the synthetic clock signal is derived from a synthetic ECG.

6. The method as claimed in claim 1, wherein the prescribed image area for calculating the correlation values exclusively comprises the heart region.

7. The method as claimed in claim 1, wherein the prescribed image area is determined by a pattern recognition method and for calculating the correlation values exclusively comprises the heart region.

8. The method as claimed in claim 1, wherein the method is used in conjunction with spiral scanning.

9. The method as claimed in claim 1, wherein the method is used in conjunction with sequential scanning.

10. The method as claimed in claim 1, wherein for the final reconstruction per heart cycle, at least one image plane of respectively completed detector data is extracted from said heart cycle, and said image plane is reconstructed to form a volume data record.

11. The method as claimed in claim 1, wherein for the final reconstruction, incomplete detector data from a number of cardiac cycles are combined to form completed detector data, and the volume data records are subsequently reconstructed therefrom.

12. The method as claimed in claim 1, wherein for the final reconstruction, incomplete detector data from a number of cardiac cycles are reconstructed to form incomplete image data and are subsequently combined to form complete image data.

13. The method as claimed in claim 1, wherein the synthetic clock signal is derived from a clock generator.

14. A spiral scanning method, comprising the method as claimed in claim 1.

15. A sequential scanning method, comprising the method as claimed in claim 1.

16. A computed tomography unit for taking X-ray CT pictures of a patient's beating heart, comprising:
   an apparatus for rotating scanning of the patient having at least one X-ray source and at least one detector that continuously detects attenuation of the X-rays and outputs detected data to a control and arithmetic unit;
   means for generating a synthetic clock signal, that is not based on signals derived from the patient's beating heart, with a frequency that corresponds to a typical patient's heart rate;
   means for reconstructing test volume data records of the heart during a complete scan and during each cycle phase of the synthetic clock signal at a number of different phases of the synthetic clock, each test volume data record being associated with its respective phase and its z-position;
   means for calculating correlation values between temporally and spatially neighboring test volume data records over a prescribed image area and insertion in a spatiotemporal matrix for searching for maxima of the correlation values; and means for calculating final volume data records from the detector data records from which the test volume data records that have led to correlation maxima originate, and for outputting the calculated final volume data records as a three-dimensional pictorial illustration.

17. A computed tomography unit in accordance with claim 16, wherein the specified means include a system of at least one arithmetic unit and programs or program modules that execute the claimed functions.

18. A computer readable medium including program segments for, when executed on a computer device, causing the computer device to implement the method of claim 1.

* * * * *